United States Patent
Doan et al.

(10) Patent No.: US 11,911,624 B2
(45) Date of Patent: Feb. 27, 2024

(54) LOGGING THE EXECUTION OF SUB-PROGRAMS WITHIN A STIMULATION PROGRAM FOR AN IMPLANTABLE STIMULATOR DEVICE

(71) Applicant: Boston Scientific Neuromodulation Corporation, Valencia, CA (US)

(72) Inventors: Que Doan, West Hills, CA (US); Sridhar Kothandaraman, Valencia, CA (US); Adam Featherstone, Meridian, ID (US); Dennis Vansickle, Lancaster, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 102 days.

(21) Appl. No.: 17/450,365

(22) Filed: Oct. 8, 2021

(65) Prior Publication Data

US 2022/0023648 A1    Jan. 27, 2022

Related U.S. Application Data

(63) Continuation of application No. 16/419,879, filed on May 22, 2019, now Pat. No. 11,160,987.

(Continued)

(51) Int. Cl.
     *A61N 1/372*      (2006.01)
     *A61N 1/36*      (2006.01)

(52) U.S. Cl.
     CPC ....... *A61N 1/37235* (2013.01); *A61N 1/3605* (2013.01); *A61N 1/36071* (2013.01);

(Continued)

(58) Field of Classification Search
     CPC .............. A61N 1/3605; A61N 1/36071; A61N 1/36164; A61N 1/36167; A61N 1/37241;
(Continued)

(56) References Cited

U.S. PATENT DOCUMENTS 6,181,969 B1    1/2001   Gord
6,516,227 B1    2/2003   Meadows et al.
(Continued)

OTHER PUBLICATIONS

International Search Report and Written Opinion regarding corresponding PCT Application No. PCT/US2019/033583, dated Aug. 5, 2019.

*Primary Examiner* — Paula J Stice
(74) *Attorney, Agent, or Firm* — Lewis & Reese, PLLC

(57) ABSTRACT

An implantable stimulator device is disclosed for executing a stimulation program comprising a plurality of sub-programs, wherein the sub-programs are configured to be automatically sequentially executed by stimulation circuitry in the device. Control circuitry periodically stores log data to indicate where each sub-program is in its execution. If the device experiences an interruption that prevents the stimulation circuitry from executing the stimulation program, and upon receiving an indication that the stimulation circuitry can continue execution of the stimulation program, the control circuitry is configured to query the log data to determine a sub-program during which the interruption occurred, and using the log data, cause the stimulation circuitry to continue execution of the stimulation circuitry either at the beginning of the sub-program, or at a point during the sub-program when the interruption occurred.

12 Claims, 9 Drawing Sheets

Related U.S. Application Data

(60) Provisional application No. 62/748,031, filed on Oct. 19, 2018, provisional application No. 62/680,539, filed on Jun. 4, 2018.

(52) U.S. Cl.
CPC ..... *A61N 1/36157* (2013.01); *A61N 1/36164* (2013.01); *A61N 1/36167* (2013.01); *A61N 1/37223* (2013.01); *A61N 1/37241* (2013.01)

(58) Field of Classification Search
CPC ............ A61N 1/36062; A61N 1/36132; A61N 1/3628; A61N 1/36128; A61N 1/36
See application file for complete search history.

(56) References Cited

U.S. PATENT DOCUMENTS

| | | | |
|---|---|---|---|
| 7,373,206 B2 | 5/2008 | Sieracki et al. | |
| 8,065,019 B2 | 11/2011 | Marnfeldt et al. | |
| 8,473,070 B2 | 6/2013 | Marnfeldt et al. | |
| 8,606,362 B2 | 12/2013 | He et al. | |
| 8,620,436 B2 | 12/2013 | Parramon et al. | |
| 9,259,574 B2 | 2/2016 | Aghassian et al. | |
| 9,731,133 B1 | 8/2017 | Thacker et al. | |
| 2008/0319497 A1 | 12/2008 | Griffith et al. | |
| 2010/0114204 A1 | 5/2010 | Burnes et al. | |
| 2012/0095529 A1 | 4/2012 | Parramon et al. | |
| 2015/0165209 A1 | 6/2015 | Grandhe et al. | |
| 2015/0231402 A1 | 8/2015 | Aghassian | |
| 2015/0360038 A1 | 12/2015 | Zottola et al. | |
| 2016/0144183 A1 | 5/2016 | Marnfeldt | |
| 2017/0080234 A1* | 3/2017 | Gillespie | A61N 1/37247 |
| 2017/0173335 A1* | 6/2017 | Min | A61N 1/0551 |
| 2017/0189683 A1 | 7/2017 | Perryman et al. | |
| 2017/0361113 A1 | 12/2017 | Aghassian et al. | |
| 2018/0071513 A1 | 3/2018 | Weiss et al. | |
| 2018/0071516 A1 | 3/2018 | Weiss et al. | |
| 2018/0071520 A1 | 3/2018 | Weerakoon et al. | |
| 2019/0046800 A1 | 2/2019 | Doan et al. | |
| 2019/0083796 A1 | 3/2019 | Weerakoon et al. | |
| 2019/0175915 A1 | 6/2019 | Brill et al. | |
| 2019/0209844 A1 | 7/2019 | Esteller et al. | |
| 2019/0344081 A1 | 11/2019 | Moffitt | |

\* cited by examiner

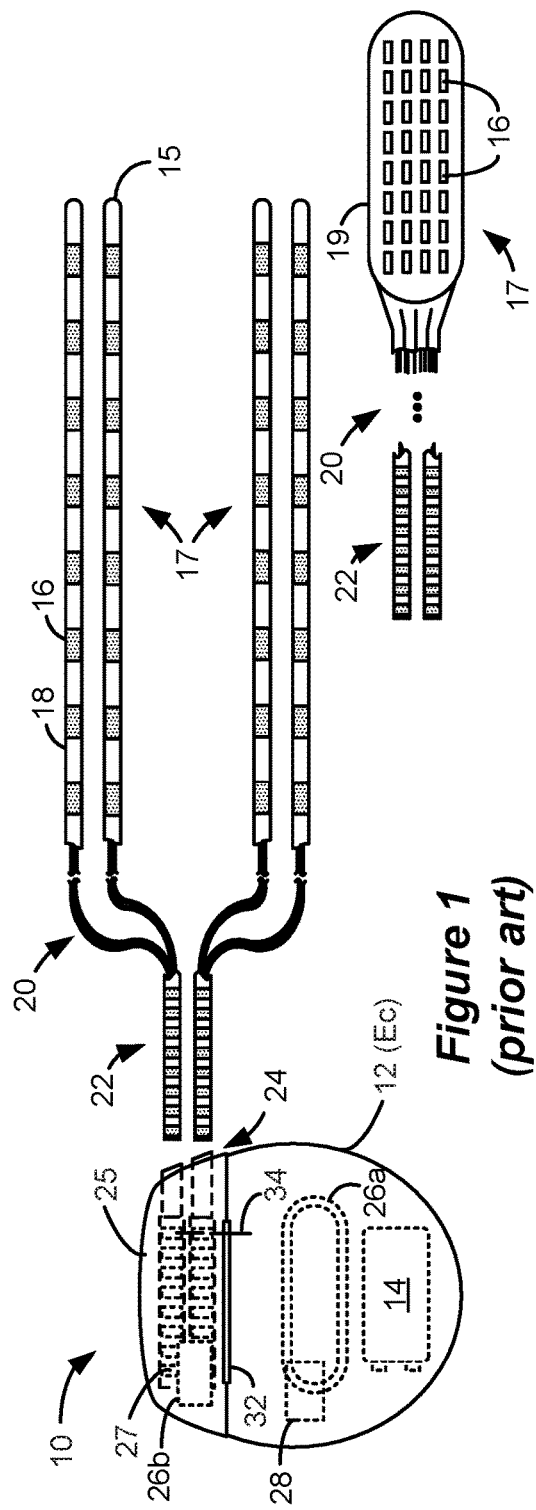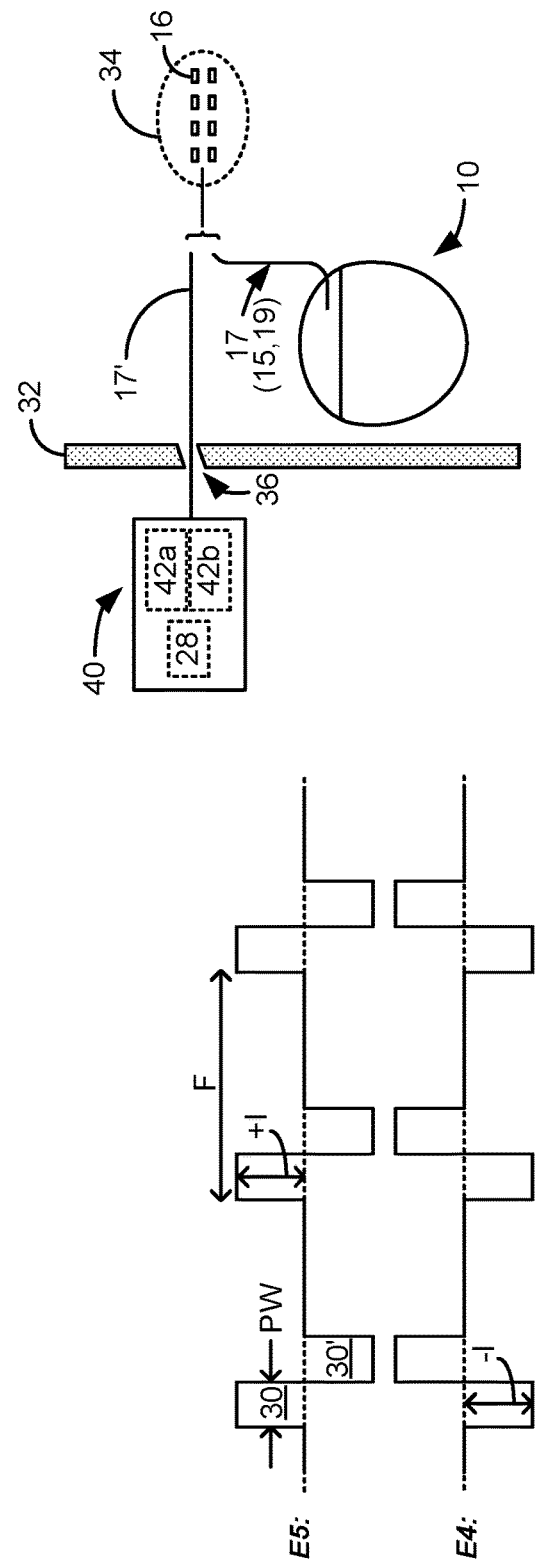

LOGGING THE EXECUTION OF SUB-PROGRAMS WITHIN A STIMULATION PROGRAM FOR AN IMPLANTABLE STIMULATOR DEVICE

CROSS REFERENCE TO RELATED APPLICATIONS

This is a continuation of U.S. patent application Ser. No. 16/419,879, filed May 22, 2019 (now U.S. Pat. No. 11,160,987), which is a non-provisional application of U.S. Provisional Patent Application Serial Nos. 62/748,031, filed Oct. 19, 2018, and 62/680,539, filed Jun. 4, 2018. Priority is claimed to these applications, and they are incorporated herein by reference.

FIELD OF THE INVENTION

This application relates to Implantable Medical Devices (IMDs), and more specifically to techniques for logging the execution of sub-programs within a stimulation program for an implantable stimulator device such as an Implantable Pulse Generator (IPG) or an External Trial Stimulator (ETS).

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to tissue-stimulating electrodes 16 via one or more electrode leads that form an electrode array 17. For example, one or more percutaneous leads 15 can be used, in which ring-shaped or split-ring electrodes 16 are carried on a flexible body 18, which also houses the individual lead wires 20 coupled to each electrode 16. In another example, a paddle lead 19 having electrodes 16 positioned on one of its generally flat surfaces also forms an electrode array 17. The lead wires 20 are coupled to proximal contacts 22, which are insertable into lead connectors 24 fixed in a header 25 on the IPG 10, which header can comprise an epoxy for example. Once inserted, the proximal contacts 22 connect to header contacts 27 within the lead connectors 24, which are in turn coupled by feedthrough pins 34 through a case feedthrough 32 to circuitry within the case 12, although these details aren't shown.

In the illustrated IPG 10, there are thirty-two electrodes (E1-E32), split between four percutaneous leads 15, or contained on a single paddle lead 19, and thus the header 25 may include a 2×2 array of eight-electrode lead connectors 24. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning the left and right of the patient's spinal column. The proximal contacts 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected the case 12 in other IPG solutions. The goal of SCS therapy is to provide electrical stimulation from the electrodes 16 to alleviate a patient's symptoms, such as chronic back pain for example.

IPG 10 can include an antenna 26a allowing it to communicate bi-directionally with a number of external devices discussed subsequently. Antenna 26a as shown comprises a conductive coil within the case 12, although the coil antenna 26a can also appear in the header 25. When antenna 26a is configured as a coil, communication with external devices preferably occurs using near-field magnetic induction. IPG 10 may also include a Radio-Frequency (RF) antenna 26b. In FIG. 1, RF antenna 26b is shown within the header 25, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (current I, although a voltage amplitude V can also be used); the frequency (F) and pulse width (PW) of the pulses; the electrodes 16 activated to provide such stimulation; and the polarity of such active electrodes, i.e., whether active electrodes are to act as anodes that source current to the tissue or cathodes that sink current from the tissue. These and possibly other stimulation parameters taken together comprise a stimulation program that the IPG 10 can execute to provide therapeutic stimulation to a patient.

In the example of FIG. 2, electrode E5 has been selected as an anode (during its first phase 30), and thus provides pulses which source a positive current of amplitude +I to the tissue. Electrode E4 has been selected as a cathode (again during first phase 30), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time, as discussed subsequently.

The pulses as shown in FIG. 2 are biphasic, comprising a first phase 30, followed quickly thereafter by a second phase 30' of opposite polarity. As is known, use of a biphasic pulse is useful in active charge recovery. See, e.g., U.S. Patent Application Publication 2016/0144183. In the example shown, the first and second phases 30 and 30' have the same duration and amplitude (although of opposite polarities), which ensures the same amount of charge during both phases, and thus hopefully full recovery of charge on any capacitance in the current paths. However, the second phase 30' may also be charged balance with the first phase 30 if the product of the amplitude and durations of the two phases are equal, as is well known. The width of each pulse, PW, is shown as comprising the duration of first pulse phase 30, although pulse width could also refer to the total duration of the first and second pulse phases 30 and 30' as well. Although not shown in FIG. 2, an interphase period during which no current is driven can intervene between the first and second phases 30 and 30'.

IPG 10 includes stimulation circuitry 28 (FIG. 1) that can be programmed to produce the stimulation pulses at the electrodes as defined by the stimulation program. Stimulation circuitry 28 can for example comprise the circuitry described in U.S. Patent Application Publications 2018/0071513 and 2018/0071520, or in U.S. Pat. Nos. 8,606,362 and 8,620,436. These references are incorporated herein by reference in their entireties.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue 32 at a target location 34, such as within the spinal column as explained earlier. The proximal ends of the trial electrode arrays(s) 17' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., a few weeks), which allows the patient and his clinician to experiment with different stimulation parameters to try and find a stimulation program that alleviates the patient's symptoms (e.g., pain). If external trial stimulation proves successful, trial electrode arrays 17' are explanted, and a full IPG 10 and a permanent electrode array 17 (e.g., one or more percutaneous 15 or paddle 19 lead(s)) are implanted as described above; if unsuccessful, the trial electrode array 17' is simply explanted.

Like the IPG 10, the ETS 40 can include one or more antennas to enable bi-directional communications with external devices, as shown in FIG. 4. Such antennas can include a near-field magnetic-induction coil antenna 42a, and/or a far-field RF antenna 42b, as described earlier. ETS 40 may also include stimulation circuitry able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 to produce stimulation with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, preferably including means for entering commands (e.g., buttons 49 or selectable graphical icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which are capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

Control circuitries 48 and 70 in the external controller 45 and clinician programmer 50 can comprise one or more microprocessors, microcomputers, Digital Signal Processors (DSPs), FPGAs, or other circuitry capable of executing programs in a computing device. In one example, control circuitries 48 and 70 may include or be functionally equivalent to any of the i5 processors manufactured by Intel Corp., as described at https://www.intel.com/content/www/us/en/products/processors/core/i5-processors.html, and may contain computer readable media (e.g., solid state memories) for storing instructions to implement their functionalities.

SUMMARY

A stimulator device is disclosed. According to some embodiments, the stimulator device comprises a plurality of electrode nodes, each electrode node configured to be coupled to one of a plurality of electrodes configured to contact a patient's tissue. According to some embodiments, the stimulator device comprises stimulation circuitry configured to execute a stimulation program to provide a stimulation current to at least two of the electrode nodes, wherein the stimulation program comprises a plurality of sub-programs configured to be executed by the stimulation circuitry. According to some embodiments, the stimulator device comprises controller circuitry configured to periodically store information that indicates where the stimulation circuitry is in its execution of the plurality of sub-programs, and if the stimulator device experiences an interruption that prevents the stimulation circuitry from continuing execution of the plurality of sub-programs, use the stored information to continue execution of the plurality of sub-programs at a point corresponding to the interruption. According to some embodiments, the information comprises markers that are pre-defined in the stimulation program. According to some embodiments, the stimulation program comprises at least one block comprising at least one of the sub-programs, and wherein the point corresponding to the interruption comprises a beginning of a first marked sub-program in the at least one block executed when the interruption occurred. According to some embodiments, the information comprises markers that are pre-defined for at least some of the sub-programs, and wherein the point corresponding to the interruption comprises (i) a beginning of a marked sub-program that immediately precedes the sub-program executed when the interruption occurred, or (ii) if the sub-program executed when the interruption occurred is marked, at the beginning of that sub-program. According to some embodiments, the point corresponding to the interruption comprises a beginning of a sub-program executed when the interruption occurred. According to some embodiments, the point corresponding to the interruption comprises a point during the sub-program executed when the interruption occurred. According to some embodiments, the plurality of sub-programs in the stimulation program are configured to be executed sequentially by the stimulation circuitry. According to some embodiments, the controller circuitry is further configured to receive an indication that the stimulation circuitry can continue the execution of the plurality of sub-programs before using the stored information to continue execution of the plurality of sub-programs. According to some embodiments, the indication is automatically generated by the controller circuitry upon removal of an action that caused the interruption. According to some embodiments, the indication is received from an external device in communication with the stimulator device. According to some embodiments, each of the sub-programs selects a different combination of the at least two of the electrode nodes to provide the stimulation current. According to some embodiments, at least some of the different combinations of the at least two electrode nodes comprise bipoles. According to some embodiments, an amplitude of the stimulation current is different during at least some of the sub-programs. According to some embodiments, the stimulation current is sub-threshold during at least some of the sub-programs. According to some embodiments, the interruption is caused by an action comprising one or more of: a depletion of a battery in the stimulator device; a receipt at the stimulator device of an emergency shutdown signal; a change to a new stimulation program; or a pausing of the stimulation program. According to some embodiments, the stimulation device can further comprise one or more implantable leads comprising the plurality of electrodes. According to some embodiments, the stimulator device comprises a fully-implantable pulse generator. According to some embodiments, the stimulator device comprises an external trial stimulator. According to some embodiments, the information that indicates where the stimulation circuitry is in its execution of the plurality of sub-programs comprises information regarding a sub-program that is currently being executed. According to some embodiments, the information that indicates where the stimulation circuitry is in its execution of the plurality of sub-programs comprises information indicating how far a currently-executed one of the sub-programs is towards its completion. According to some embodiments, each of the sub-programs is configured to be executed for a same duration. According to some embodiments, the controller circuitry further comprises or is associated with a pain score memory, wherein the pain score memory is configured to store an association of a pain score wirelessly received at the device with an indication of a sub-program that was being executed at the time the pain score was wirelessly received. According to some embodiments, the controller circuitry further comprises or is associated with a program memory configured to store the stimulation program including each of the plurality of sub-programs. According to some embodiments, the program memory is further configured to store a duration of each sub-program.

A stimulator device is disclosed. According to some embodiments, the stimulator device comprises a plurality of electrode nodes, each electrode node configured to be coupled to one of a plurality of electrodes configured to contact a patient's tissue. According to some embodiments, the stimulator device comprises stimulation circuitry configured to execute a plurality of stimulation programs that each provide a stimulation current to at least one of the electrode nodes, wherein the plurality of stimulation programs are configured to be executed by the stimulation circuitry. According to some embodiments, the stimulator device comprises controller circuitry configured to periodically store information corresponding to execution of at least some of the plurality of stimulation programs. According to some embodiments, the controller circuitry is configured to, in response to determining that the stimulation circuitry has experienced an interruption to the execution of the plurality of stimulation programs, use the stored information to continue the execution of the plurality of stimulation programs at a point corresponding to the interruption. According to some embodiments, the information comprises markers that are pre-defined in the stimulation program. According to some embodiments, the point corresponding to the interruption comprises a point in the stimulation program corresponding to a first immediately-preceding marker in the stimulation program. According to some embodiments, the stimulation program comprises at least one block comprising at least one sub-program, and wherein the point corresponding to the interruption comprises a beginning of a first marked sub-program in the at least one block executed when the interruption occurred. According to some embodiments, the stimulation program comprises a plurality of sub-programs, wherein the information comprises markers that are pre-defined for at least some of the sub-programs, and wherein the point corresponding to the interruption comprises (i) a beginning of a marked sub-program that immediately precedes the sub-program executed when the interruption occurred, or (ii) if the sub-program executed when the interruption occurred is marked, at the beginning of that sub-program. According to some embodiments, the point corresponding to the interruption comprises a beginning of a stimulation program executed when the interruption occurred. According to some embodiments, the point corresponding to the interruption comprises a point during the stimulation program executed when the interruption occurred. According to some embodiments, the plurality of stimulation programs are configured to be executed sequentially by the stimulation circuitry. According to some embodiments, the controller circuitry is further configured to receive an indication to continue the execution of the plurality of stimulation programs before using the stored information to continue execution of the plurality of stimulation programs. According to some embodiments, the indication is automatically generated by the controller circuitry upon removal of the interruption. According to some embodiments, the indication is received from an external device in communication with the stimulator device. According to some embodiments, each of the stimulation programs selects a different combination of at least two of the electrode nodes to provide the stimulation current. According to some embodiments, at least some of the different combinations of the at least two electrode nodes comprise bipoles. According to some embodiments, an amplitude of the stimulation current is different during at least some of the stimulation programs. According to some embodiments, the stimulation current is sub-threshold during at least some of the stimulation programs. According to some embodiments, the interruption is caused by an action comprising one or more of: a depletion of a battery in the stimulator device; a receipt at the stimulator device of an emergency shutdown signal; a change to a new stimulation program; or a pausing of the stimulation program. According to some embodiments, the stimulator device further comprises one or more implantable leads comprising the plurality of electrodes. According to some embodiments, the stimulator device comprises a fully-implantable pulse generator. According to some embodiments, the stimulator device comprises an external trial stimulator. According to some embodiments, the information corresponding to execution of at least some of the plurality of stimulation programs comprises information regarding a stimulation program that is currently being executed. According to some embodiments, the information corresponding to execution of at least some of the plurality of stimulation programs comprises information indicating how far a currently-executed one of the stimulation programs is towards its completion. According to some embodiments, each of the stimulation programs is configured to be executed for a same duration. According to some embodiments, the controller circuitry further comprises or is associated with a pain score memory, wherein the pain score memory is configured to store an association of a pain score wirelessly received at the device with an indication of a stimulation program that was being executed at the time the pain score was wirelessly received.

A method for operating a stimulator device is disclosed. According to some embodiments, the stimulator device comprises a plurality of electrode nodes, each electrode node configured to be coupled to one of a plurality of electrodes configured to contact a patient's tissue, the method comprising. According to some embodiments, the method comprises causing stimulation circuitry in the stimulator device to execute a stimulation program to provide a stimulation current to at least two of the electrode nodes, wherein the stimulation program comprises a plurality of sub-programs sequentially executed by the stimulation circuitry. According to some embodiments, the method comprises periodically storing in the stimulator device information that indicates where the stimulation circuitry is in its execution of the plurality of sub-programs. According to some embodiments, the method comprises, when the stimulator device experiences an interruption that prevents the stimulation circuitry from continuing execution of the plurality of sub-programs, using the stored information to continue execution of the plurality of sub-programs at a point corresponding to the interruption. According to some embodiments, the information comprises markers that are pre-defined in the stimulation program. According to some embodiments, the stimulation program comprises at least one block comprising at least one of the sub-programs, and wherein the point corresponding to the interruption comprises a beginning of a first marked sub-program in the at least one block executed when the interruption occurred. According to some embodiments, the information comprises markers that are pre-defined for at least some of the sub-programs, and wherein the point corresponding to the interruption comprises (i) a beginning of a marked sub-program that immediately precedes the sub-program executed when the interruption occurred, or (ii) if the sub-program executed when the interruption occurred is marked, at the beginning of that sub-program. According to some embodiments, the point corresponding to the interruption comprises a beginning of a sub-program executed when the interruption occurred. According to some embodiments, the point corresponding to the interruption comprises a point during the sub-program executed when the interruption occurred. According to some embodiments, the method further comprises receiving an indication that the stimulation circuitry can continue the execution of the plurality of sub-programs before using the stored information to continue execution of the plurality of sub-programs. According to some embodiments, the indication is automatically generated upon removal of an action that caused the interruption. According to some embodiments, each of the sub-programs selects a different combination of the at least two of the electrode nodes to provide the stimulation current. According to some embodiments, at least some of the different combinations of the at least two electrode nodes comprise bipoles. According to some embodiments, the stimulation current is sub-threshold during at least some of the sub-programs. According to some embodiments, the interruption is caused by an action comprising one or more of: a depletion of a battery in the stimulator device; a receipt at the stimulator device of an emergency shutdown signal; a change to a new stimulation program; or a pausing of the stimulation program. According to some embodiments, the information that indicates where the stimulation circuitry is in its execution of the plurality of sub-programs comprises information regarding a sub-program that is currently being executed. According to some embodiments, the information that indicates where the stimulation circuitry is in its execution of the plurality of sub-programs comprises information indicating how far a currently-executed one of the sub-programs is towards its completion. According to some embodiments, each of the sub-programs is executed for a same duration. According to some embodiments, the method further comprises storing in the stimulator device a pain score with an indication of a sub-program that was being executed at the time the pain score was received.

A non-transitory computer readable medium for an external device configured to communicate with a stimulator device is disclosed. According to some embodiments, the computer readable medium includes instructions that when executed on the external device cause the external device to generate a graphical user interface (GUI) on the external device. According to some embodiments, the GUI is configured to receive one or more inputs to define a stimulation program to be executed by the stimulator device, wherein the stimulation program provides a stimulation current to at least two electrode nodes of the stimulator device, wherein the stimulation program comprises a plurality of sub-programs configured to be sequentially executed by stimulation circuitry of the stimulator device. According to some embodiments, the GUI is configured to receive one or more inputs mark at least some of the sub-programs with a marker, thereby forming one or more markers. According to some embodiments, the GUI or the external device is configured to transmit the stimulation program with the one or more markers to the stimulator device for execution. According to some embodiments, the one or more markers are configured to inform the stimulator device where to continue execution of the stimulation program when the stimulator device experiences an interruption. According to some embodiments, the one or more markers will inform the stimulator device to continue execution (i) at a beginning of a marked sub-program that immediately precedes the sub-program executed when the interruption occurred, or (ii) if the sub-program executed when the interruption occurred is marked, at the beginning of that sub-program. The non-transitory computer readable medium may also contain instructions that when executed perform other method steps described above.

BRIEF DESCRIPTION OF THE DRAWINGS

FIG. 1 shows an Implantable Pulse Generator (IPG), in accordance with the prior art.

FIG. 2 shows an example of stimulation pulses producible by the IPG or an External Trail Stimulator (ETS), in accordance with the prior art.

FIG. 3 shows use of an External Trial Stimulator (ETS) useable to provide stimulation before implantation of an IPG, in accordance with the prior art.

FIG. 5 also shows use of an external controller to rate a patient's pain during the execution of each of the sub-programs.

FIG. 6 also shows actions that can cause execution of the stimulation program to be interrupted.

DETAILED DESCRIPTION

In an SCS application, it is desirable to determine a stimulation program that will be effective for each patient to relieve their symptoms, such as pain. A significant part of determining an effective stimulation program is to determine the electrodes in the array 17 or 17' that should be selected to provide the stimulation. The neural site at which pain originates in a patient, and therefore electrodes proximate to such neural site, can be difficult to determine, and experimentation is typically undertaken to select the best combination of electrodes to provide a patient's therapy.

SCS traditionally provides a sensation of paresthesia to a patient—i.e., a tingling, prickling or heating sensation. Selecting electrodes for a given patient can be easier when paresthesia is present, because the patient can provide feedback to the clinician concerning when the paresthesia seems to "covering" the area that is causing pain. In short, the patient can generally assess when the sensation of paresthesia seems to have taken the place of the sensation of pain, which assists in electrode selection.

However, newer SCS stimulation paradigms can provide symptom relief without the sensation of paresthesia, which is often called sub-threshold stimulation therapy. See, e.g., U.S. Patent Application Publication 2019/0046800. Electrode selection for a given patient can be more difficult when paresthesia is not present, because the patient does not feel the stimulation, and therefore it can be difficult for the patient to feel whether the stimulation is covering his pain. Further, sub-threshold stimulation therapy may require a "wash in" period before it can become effective. A wash in period can take up to a day or more, and therefore sub-threshold stimulation may not be immediately effective, making electrode selection more difficult.

Figure 5:
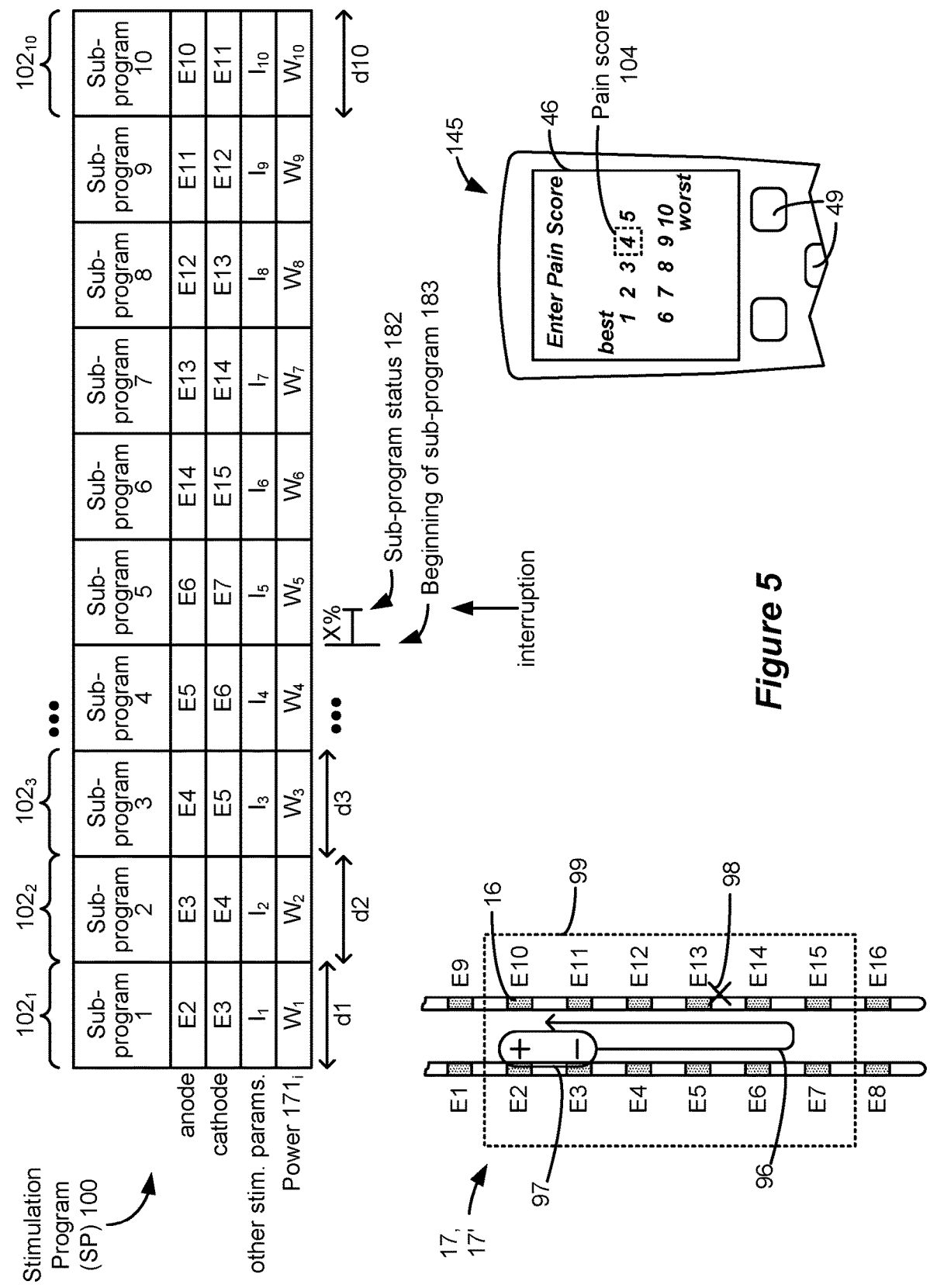
FIG. 5 shows a stimulation program for an IPG or ETS comprising a plurality of sequentially-executable sub-programs each preferably selecting a bipole for stimulation.

FIG. 5 shows a stimulation program (SP) 100 that can be executed by an IPG 110 or ETS 140 (FIG. 6) to assist in selecting electrodes for a patient, which is particularly useful when sub-threshold stimulation therapy is being provided by the IPG or ETS. Stimulation program 100 is particularly useful in a trial setting after a patient is first implanted with an electrode array 17 or 17', i.e., after receiving their IPG 110 or ETS 140.

As shown, stimulation program 100 is comprised of a sequence of sub-programs 102, each of which preferably selects different electrodes for stimulation. In the example shown, it is assumed that a site 98 of a patient's pain is likely within a tissue region 99. Such region 99 may be deduced by a clinician based on the patient symptoms, e.g., by understanding which electrodes are proximate to certain vertebrae (not shown), such as within the T9-T10 interspace. In the example shown, region 99 is bounded by electrodes E2, E7, E15, and E10, meaning that electrodes outside of this region (e.g., E1, E8, E9, E16) are unlikely to have an effect on the patient's symptoms. Therefore, these electrodes are not selected during any of the sub-programs $102_i$ to reduce the size and total duration of the stimulation program 100. In another example, sub-programs $102_i$ could be constructed for each of the electrodes without regard to a tissue region 99.

In the illustrated example, each sub-program $102_i$ of the stimulation program 100 selects two electrodes—a bipole 97—for stimulation. For example, in sub-program 1 $102_1$, electrode E2 is selected as an anode that will source a positive current ($+I_1$) to the patient's tissue, while electrode E3 is selected as a cathode that will sink a negative current ($-I_1$) from the patient's tissue. This is similar to what was illustrated earlier with respect to FIG. 2, and biphasic stimulation pulses can be used. This sub-program $102_1$ will be executed by the IPG 110 or ETS 140 for a duration d1. At the end of this duration, and as execution of the stimulation program 100 continues, the IPG 110 or ETS 140 begins executing sub-program $102_2$ for a duration d2. Preferably, sub-program $102_2$ selects a different combination of electrodes (anode electrode E3, cathode electrode E4), which moves the location of the bipole 97 in the patient's tissue. In the example shown, the sub-programs $102_i$ in the stimulation program 100 move the bipole 97 down one electrode lead, and up the other, as shown by path 96.

The goal of moving the bipole 97 along path 96, or changing the selected electrodes in each sub-program $102_i$ more generally, is to try and find an electrode selection that best covers the site 98 of the patient's pain. In the example of FIG. 5, given the site of pain 98's proximity to electrodes E13 and E14, it might be expected that sub-program 7 ($102_7$) will provide the best relief for the patient.

Note that each sub-program $102_i$ is itself a fully-executable stimulation program, specifying all relevant stimulation parameters, such as amplitude I, frequency f, pulse width PW, although not all of these stimulation parameters are shown in FIG. 5. In one example, stimulation parameters I, f, and PW can be the same in each sub-program $102_i$, with the sub-programs $102_i$ differing only in the selected electrodes and their polarities. However, this is not strictly required, and any one or more stimulation parameters can be changed in each stimulation program $102_i$. One stimulation parameter of interest, amplitude $I_i$, is shown because it may be useful to titrate this value for each sub-program $102_i$. Titrating the amplitude $I_i$ for each sub-program $102_i$ is useful especially when sub-threshold therapy is to be provided during each sub-program $102_i$. Given the difference in the patient's tissue proximate to each electrode, a suitable sub-threshold amplitude $I_i$ may need to be varied. For example, a current of amplitude $I_3$=4 mA may be just below what the patient can sense when bipole E4/E5 is selected during sub-program $102_3$, and hence is suitable. However, this current amplitude may be too high—i.e., may be sensed by the patient—when bipole E5/E6 is selected during sub-program $102_4$. Therefore the amplitude during this sub-program $102_4$ may be lowered to $I_4$=3.5 mA for example.

It is not necessary that the selected electrodes in each sub-program $102_i$ comprise bipoles as shown. More complicated electrode selections (e.g., three-electrode tripoles, or electrode combinations spanning the leads) could also be made. Further, the selected electrodes need not comprise physical bipoles defined at two physical electrodes 16. Instead, virtual bipoles (or tripoles, etc.), can be formed in which the pole positions are not necessarily formed at the location of the physical electrodes. See, e.g., U.S. Pat. No. 10,881,859, discussing virtual poles in an implantable stimulator device.

To summarize, as the goal of stimulation program 100 is to try and find one or more sub-programs $102_i$ that provide good therapy for a patient, the sub-programs $102_i$ can comprise randomly different stimulation programs. That is, any one or more stimulation parameters—selected electrodes, their polarities, amplitude, frequency, pulse width, etc.—can be varied or remain the same during each of the sub-programs. Nonetheless, sub-programs $102_i$ providing physical bipoles 97 moving step-wise along a path 96 provide a good example, as well as a logical use model designed to assist the patient or clinician in finding a "sweet spot" at which pain 98 is present in the patient's tissue. However, the technique is not limited to this use model.

Stimulation program 100 is preferably formed at the clinician programmer 150 (FIG. 6), although it may also be formed at any external device in communication with the IPG 110 or ETS 140, such as a patient external controller 145. When forming the stimulation program 100, each sub-program $102_i$ is defined using the Graphical User interface (GUI) of the device, and then the sub-programs 102*i* are concatenated with their durations. Once complete, the stimulation program 100 can be wirelessly telemetered to the patient's IPG 110 or ETS 140 for execution, as explained further below.

When used in a trial setting to try and locate the site 98 of a patient's pain, the stimulation program 100 can end once its last sub-program ($102_{10}$) has been executed. Although not shown in the figures, when the stimulation program 100 reaches its end, the IPG 110 or ETS 140 can establish a communication link with the clinician program 150 or external controller 145 to notify the clinician or patient of this fact. Alternatively, the stimulation program 100 can run in a loop, executing $102_1$, $102_2$, etc. after the execution of $102_{10}$ has completed. Although not shown, the GUI of the clinician program 150 or external controller 145 can allow the clinician or patient to specify the number of loops that the stimulation program will be executed by the IPG 110 or ETS 140.

As mentioned above, sub-threshold stimulation can make therapy effectiveness difficult to immediately determine, especially if each sub-program $102_i$ must be washed in for a period. Therefore, the duration di of each sub-program $102_i$ is preferably run for a significant duration, which might comprise two to three days. Durations di are preferably the same for each of the sub-programs $102_i$, but could also be different.

To assist in gauging the effectiveness of each sub-program $102_i$, the patient may use the GUI of his external controller 145 to qualitatively rate therapy effectiveness by entering a pain score 104. This can comprise the use of a pain rating scale, such as the Numerical Rating Scale (NRS) or the Visual Analogue Scale (VAS). Such scales allow the patient to rank pain on a scale of 1 to 10, with 1 denoting no or little pain and 10 denoting a worst pain imaginable. The patient preferably enters a pain score 104 at least a few times per day, although the patient need not do so on a strict schedule. System treatment of the entered pain scores 104 is discussed further below. While this disclosure talks about the qualitative patient input of a "pain score" for simplicity, such score need not be limited to an assessment of pain, but could also be indicative of other patient statuses, such as patient wellness or therapy satisfaction. "Pain score" is used and defined herein as encompassing any patient statuses.

Also shown in FIG. 5 is a calculation of the power $W_i$ 171$_i$ that each sub-program $102_i$ will expend in the IPG 110 or ETS 140. Such power values $W_i$ can be calculated or estimated in one example by multiplying the amplitude I, the frequency f, and pulse width PW used during each sub-program $102_i$. The power values $W_i$ may also include estimations of the power expended by the IPG 110 or ETS 140 when performing functions apart from the provision of stimulation, such as the quiescent power draw of the IPG or ETS's components, power drawn during telemetry, etc. The power $W_i$ of each sub-program $102_i$ can be important to consider, as battery power in the IPG 110 or ETS 140 may be limited. Power $W_i$ may also be indicative of energy over a period of time, e.g., the power $W_i$ times the duration di of each sub-program $102_i$. The power 171$_i$ of each sub-program $102_i$ can also comprise a power actually measured in the IPG 110 or ETS 140 as each sub-program $102_i$ is executing.

Figure 6:
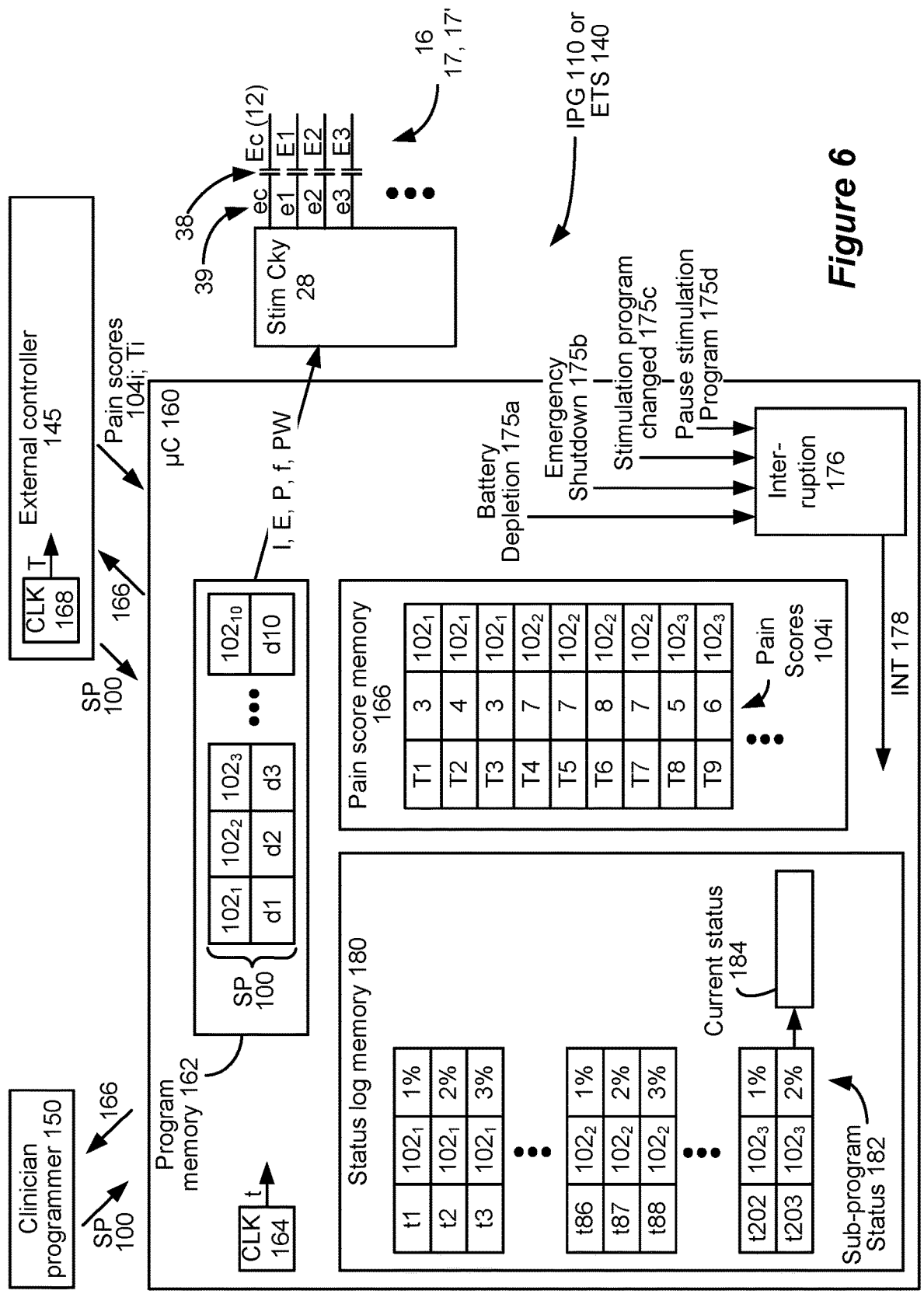
FIG. 6 shows circuitry in the IPG or ETS, and in particular shows the logging of pain scores, and logging the status of the execution of the sub-programs comprising the stimulation program.

FIG. 6 shows further details of the IPG 110 or ETS 140 in conjunction with external devices that communicate with them, such as clinician programmer 150 and patient external controller 145. IPG 110, ETS 140, clinician programmer 150 and external controller 145 may generally function and be constructed as described in Introduction, although each have additional features as described herein.

Central to the IPG 110 or ETS 140 is control circuitry 160, which in one example can comprise a microcontroller, such as Part Number MSP430, manufactured by Texas Instruments, which is described in data sheets at http://www.ti-.com/lsds/ti/microcontroller/16-bit_msp430/overview.page?DCMP=MCU_other& HQS=msp430. The control circuitry 160 more generally can comprise a microprocessor, Field Programmable Grid Array, Programmable Logic Device, Digital Signal Processor or like devices. Control circuitry 160 may include a central processing unit capable of executing instructions, with such instructions stored in volatile or non-volatile memory within or associated with the control circuitry. Control circuitry 160 may also include, operate in conjunction with, or be embedded within an Application Specific Integrated Circuit (ASIC), such as described in U.S. Patent Application Publications 2008/0319497, 2012/0095529, 2018/0071513, or 2018/0071520. The control circuitry 160 may comprise an integrated circuit with a monocrystalline substrate, or may comprise any number of such integrated circuits operating as a system. Control circuitry may also be included as part of a System-on-Chip (SoC) or a System-on-Module (SoM) which may incorporate memory devices and other digital interfaces.

Control circuitry 160 can include or interface with a program memory 162, which stores the stimulation program, such as stimulation program (SP) 100, that the IPG 110 or ETS 140 is running. As shown, the stimulation program 100, inclusive of its sub-programs $102_i$ and their durations di, can be wirelessly telemetered to the IPG 110 or ETS 140 by either the clinician program 150 or the external controller 145 and stored in the program memory 162. Although not shown, the program memory 162 can also store a number of loops that the stimulation program 100 will execute, which as noted earlier can be specified at the relevant external device.

The control circuitry 160 executes the stimulation program 100 by executing each sub-program $102_i$ sequentially, and in accordance with the duration di of each. Clock circuitry 164 with the IPG 110 or ETS 140 assists with timing and, in conjunction with the durations $d_i$, can inform the control circuitry 160 when the duration of a currently-executed sub-program $102_i$ has expired, and when execution of a next sub-program $102_{i+1}$ should begin. Clock circuitry 164 provides a timing reference t for the IPG 110 or ETS 140.

When executing each sub-program $102_i$ in the stimulation program 100, the program memory 162 passes various stimulation parameters for each sub-program $102_i$ to stimulation circuitry 28, which stimulation parameters can comprise the current amplitude (I), the electrodes (E) (e.g., the bipole 97) chosen for stimulation, the polarity (P) of the selected electrodes (whether they are to act as anodes or cathodes), and timing information including the frequency (f) and the pulse width (PW). The stimulation circuitry 28 can then form stimulation (e.g., pulses) at the selected electrodes with the correct amplitude and timing. Various examples of stimulation circuitries 28 can be found in U.S. Pat. Nos. 6,181,969, 8,606,362, 8,620,436, U.S. Patent Application Publications 2018/0071520 and 2019/0083796. Although not shown in FIG. 6, stimulation circuitry 28 may comprise a portion of the control circuitry 160.

Preferably, the pain scores $104_i$ entered by the patient using his external controller 145 (FIG. 5) are wirelessly telemetered to and stored in the IPG 110 or ETS 140, and specifically in a pain score memory 166. It is useful to know when the patient entered a particular pain score $104_i$, and so each pain score $104_i$ can be associated with a timing reference $T_i$ provided by clock circuitry 168 operating in the external controller 145. Time $T_i$ can comprise a real time clock, and can comprise a time reference different from the time t output by the clock circuitry 164 in the IPG 110 or ETS 140. However, these two timing references t and T can be synchronized when the IPG 110 or ETS 140 is in communication with the external controller 145, as explained in U.S. Pat. No. 8,065,019.

Entering a given pain score $104_i$ into the external controller 145 preferably causes the external controller 145 to initiate a communication session with the IPG 110 or ETS 140 so that the pain score $104_i$ and associated time reference $T_i$ can be immediately telemetered to the pain score memory 166 and associated with an indication of the sub-program $102_i$ that is currently being executed. However, such immediate telemetry of the pain scores $104_i$ to the IPG 110 or ETS 140 is not strictly necessary in other designs, and the pain scores $104_i$ and timing references $T_i$ can be associated with the currently-executed sub-program $102_i$ in other ways, including at the external devices 150 and 145.

Figure 4:
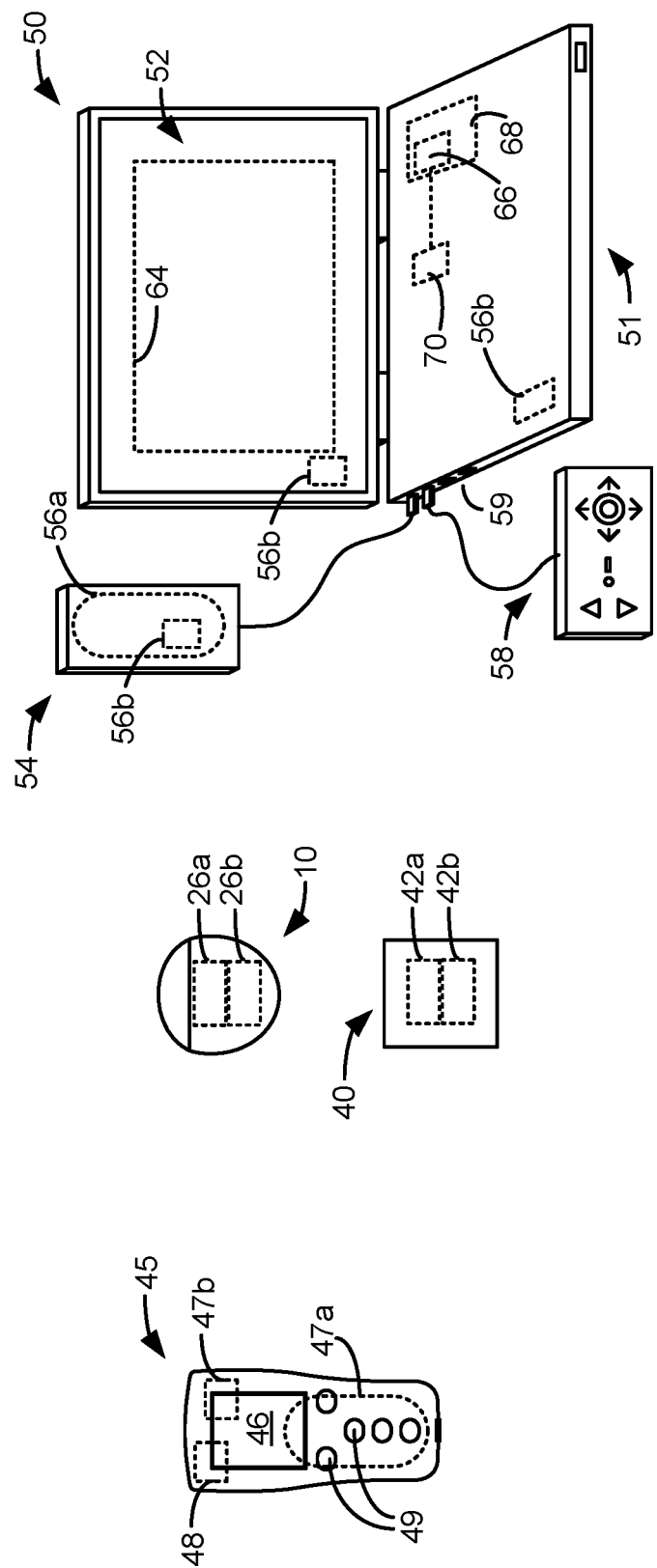
FIG. 4 shows various external devices capable of communicating with and programming stimulation in an IPG and ETS, in accordance with the prior art.
Figure 7:
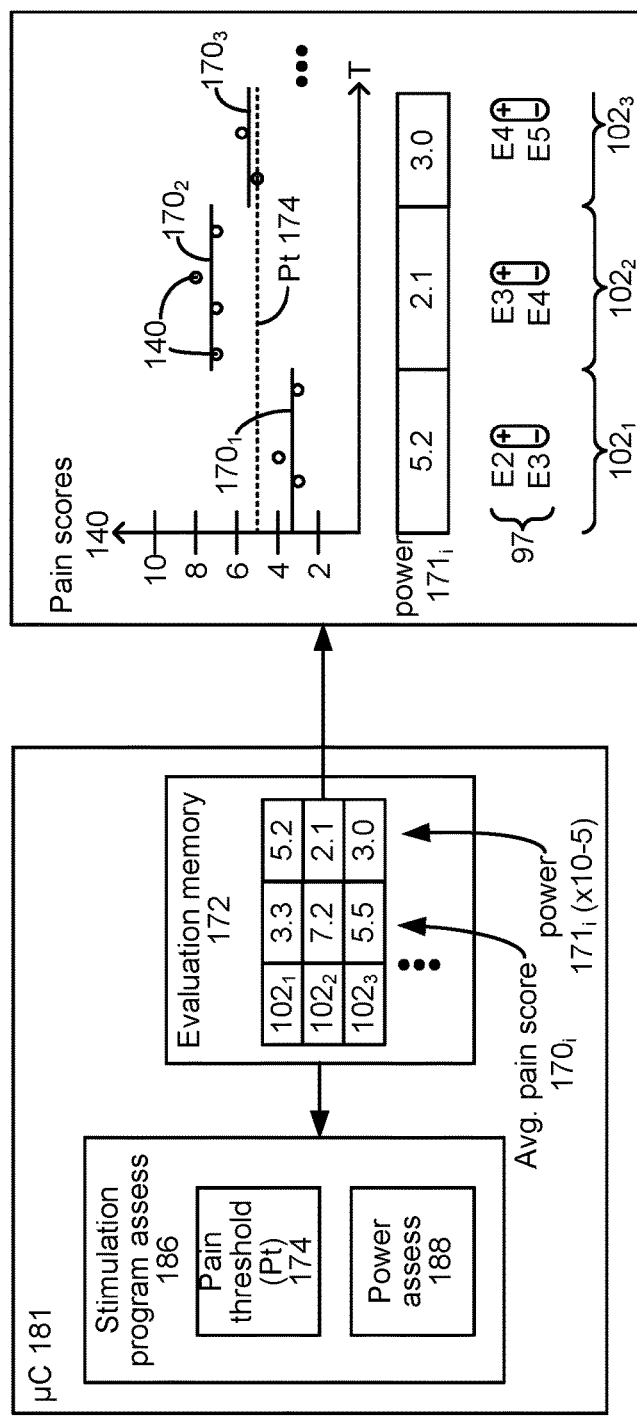
FIG. 7 shows evaluation of the pain scores and the power draw required for each sub-program, and shows how such data can be displayed on an external device in communication with the ETS or IPG.

The contents of pain score memory 166 can be read out of the IPG 110 or ETS 140 and telemetered to the clinician programmer 150 or external controller 145 for evaluation. Such evaluation can occur and be depicted at these external devices in different ways, but FIG. 7 shows one such example. FIG. 7 shows control circuitry 181 in the clinician programmer 150 or external controller 145, which may be similar to the control circuities described earlier (e.g., 48, 70, FIG. 4). The pain scores $140_i$ associated with each sub-program $102_i$ can be stored in an evaluation memory 172, and can be graphed on the displays 52 or 46 of the clinician programmer 150 or external controller 145 as shown. Alternatively, the pain scores $140_i$ for each sub-program $102_i$ can be averaged to provide an average pain score $170_i$ for each sub-program $102_i$, as shown in the memory 172. It should be noted that an average pain score $170_i$ for each sub-program $102_i$ can be calculated in different ways, and in view of different practical considerations. For example, a patient's pain may vary depending on the time of day and based on activity or patient position. There may also be aberrant data points $140_i$ that might be discarded from the pain score average $170_i$. It may also be useful to ignore any data points $140_i$ occurring early in the duration di of each sub-program $102_i$, as therapy may be washing in during that time. Thus, is not strictly necessary to include every pain score $140_i$ data point in the average $170_i$ for each sub-program $102_i$. The average pain scores $170_i$ can also be graphed as shown. Presenting the data in this or other fashions (e.g., as a list) can assist the clinician or patient to better understand which sub-program(s) $102_i$, i.e., which bipole 97 combinations, seem to work best for the patient.

Optionally included in evaluation memory 172 are the power values $171_i$ calculated for each of the sub-programs $102_i$, as discussed earlier with reference to FIG. 5. These power values may also be illustrated or graphed on the display screen 52 or 46 of the clinician programmer 150 or external controller 145. The power values $171_i$ may be scaled as is convenient, but are shown in the Figures as Watts$\times 10^{-5}$.

The data displayed in FIG. 7 assists in locating the site 98 (FIG. 5) of the patient's pain, and can be used as a basis for further experimentation. For example, in FIG. 7 it appears that sub-program $102_1$ provided the patient the best pain relief, as the (average) pain scores are lower for this sub-program. This might suggest that the site 98 of the patient's pain is proximate to electrodes E2 and E3 selected during sub-program $102_1$ (FIG. 5). Given these results, it may be sensible thereafter for the patient to use sub-program $102_1$ as his therapy going forward. Or, it may be interesting to develop a new sub-program (e.g., $102_{11}$; not shown) which changes the stimulation parameters associated with sub-program $102_1$. For example, for a new sub-program $102_{11}$, the amplitude, frequency, or pulse width of sub-program $102_1$ could be changed. Or new electrodes could be selected in the general vicinity of sub-program $102_1$'s E2/E3 bipole 97. For example, and referring briefly to FIG. 5, for a new sub-program $102_{11}$, a tripole consisting of electrodes E1/E2/E3 or E2/E3/E4 could be tried. Or electrodes on a different lead but proximate to E2 and E3 could also be tried, such as E2/E10 or E3/E11. Such new sub-program $102_{11}$ can be evaluated on its own as before—by running it for a duration d11, and having the patient enter pain scores $140_i$ during that duration, to see if the patient's pain scores can be further decreased. Alternatively, new sub-program $102_{11}$ could be manually or automatically be included in the stimulation program 100.

An issue concerning stimulation program 100 is the length of time it must run to fully complete execution and evaluation of each sub-program $102_i$. As noted earlier, given the sub-threshold nature of the therapy, and the need for a wash in period, each sub-program $102_i$ may take two to three days (di). If it is assumed that stimulation program 100 includes ten sub-programs $102_i$, it would take 20-30 days to run stimulation program 100 in its entirety.

This can be problematic because there may be various reasons, especially given the length of stimulation program 100, that execution of stimulation program 100 can be interrupted. First, the battery in the IPG 110 or ETS 140 (not shown) may deplete to a level that the IPG 110 or ETS 140 will not function. This may be because these devices have rechargeable batteries that the patient neglects to wirelessly recharge. See, e.g., U.S. Patent Application Publication 2017/0361113, describing an external charger for an implantable device. Interruption may also occur if the IPG 110 or ETS 140 detects an emergency shutdown, such as provided by an external bar magnet. See, e.g., U.S. Pat. No. 8,473,070, describing emergency shutdown of an implantable device. Interruption of the stimulation program 100 may also occur simply because the clinician or patient uses an external device 145 or 150 to change the stimulation program, perhaps to temporarily try different stimulation parameters. Interruption of the stimulation program 100 may also occur because an external device 145 or 150 is used to pause the stimulation program 100. These are just non-limiting examples of actions that can interrupt execution of stimulation program 100 in the IPG 110 or ETS 140, and others actions may cause interruption as well.

Interruption of the stimulation program 100 raises the concern that the entire stimulation program 100 might need to be run again from its beginning. This is undesirable, because it would take significant time and delay evaluation of the various sub-programs $102_i$ that might be effective for the patient.

To address this, the control circuitry 160 in the IPG 110 or ETS 140 is able to detect where stimulation program 100 is in its operation, and can generally resume operation where it left off. Referring again to FIG. 6, such functionality is assisted by a status log memory 180. The status log memory 180 preferably periodically stores an indication of the sub-program $102_i$ currently being executed as well as a status 182 of that sub-program. Sub-program status 182 in this example comprises an indication of how far along the current sub-program $102_i$ is in its execution. This status can be indicated in any number of ways, but for simplicity is shown in FIG. 6 as comprising a percentage to completion (X %). The data in status log memory 180 can also be associated with a timing reference t provided by the clocking circuitry 164 in the IPG 110 or ETS 140, which again can be synchronized with the timing reference T provided in an external device if desirable. Timing reference t can be used in conjunction with the durations di to compute a percent completion value X %. Data can be logged periodically in the status log memory 180, but periodicity does not imply that data is necessarily stored at a set frequency or interval. That being said, data is preferably stored in the status log memory 180 at a set frequency, such as once an hour. Note that the various memories in the IPG 110 or ETS 140—such as 162, 166, and 180—can comprise memory addresses in a single memory within or accessible to the control circuitry 160.

While the status log memory 180 can comprise a historical log, it can be simpler to move the current status—i.e., the last logged entry—into its own memory location 184. This way, upon receiving an indication that the stimulation circuitry 28 can begin re-executing the stimulation program 100, the current status register 184 can simply be queried to know where to begin execution. In fact, status log memory 180 need not have historical log information, so long as current status register 184 is continually updated. Current status register 184 is preferably a non-volatile memory, and so will retain its data even if power to the IPG 110 or ETS 140 fails or is removed. Other memories present in the IPG 110 or ETS 140 are preferably also non-volatile memories.

An interruption logic module 176 can receive indications of the various types of actions that can interrupt execution of the stimulation program 100, and can issue an interrupt INT 178 when any relevant action has occurred. Interrupt 178 can cause the status log memory 180 to populate the current status register 184, and may also disable the program memory 162 or the stimulation circuitry 28.

Actions indicating the need to interrupt execution of the stimulation program 100 can come from different sources in the IPG 110 or ETS 140. For example, a battery deletion indicator 175a can come from battery voltage sensing circuitry (not shown), which monitors the voltage Vbat of the IPG or ETS's battery, and asserts the indicator 175 to the interruption module 176 when Vbat falls below a threshold Vt. Typically, the threshold Vt would be set just a bit higher (e.g., 0.1V more) than the voltage needed for the IPG 110 or ETS 140 to operate. This allows some time (0.1 Volts' worth) to allow the IPG 110 or ETS 140 to take appropriate shutdown steps before the IPG or ETS truly become non-functional, such as stopping stimulation, logging various IPG or ETS status data, etc.

The emergency shutdown indicator 175b can come from a magnetic Reed or Hall sensor (not shown) in the IPG 110 or ETS 140, which can be activated by placement of an emergency shutdown bar magnet in the vicinity of the IPG or ETS. Emergency shutdown may cause the IPG or ETS's circuitry to become disconnected from its battery, but before this a short delay period can be provided to allow the IPG 110 or ETS 140 to take appropriate shutdown steps. See, e.g., U.S. Pat. No. 8,473,070, explaining emergency shutdown and a shutdown delay period.

An indicator that the stimulation program has been (temporarily) changed (175c) or paused (175d) can come from the program memory 162.

When the action causing interruption is later removed, interrupt 178 will deassert. At this point, the stimulation program 100 can continue its execution. Continuing the execution of the stimulation program 100 can occur automatically in the IPG 110 or ETS 140 without patient or clinician intervention. This can occur by having the control circuitry 160 read the data in the current status register 184. As noted earlier, the current status register 184 preferably stores an indication of the sub-program $102_i$ that was being executed at the time of the interruption (e.g., sub-program $102_5$ in FIG. 5) as well as a sub-program status 182 indicative of how far along that sub-program was towards it completion (e.g., X %). The control circuitry 160 may therefore continue the execution of the stimulation program 100 by starting back at the beginning 183 of sub-program $102_5$, or using the sub-program status 182 (e.g., X %) to start at some point in the middle of sub-program $102_5$ where it left off, as shown in FIG. 5. Whether the IPG 110 or ETS 140 will automatically continue execution at the beginning 183 or in the middle 182 of the sub-program can be a feature that a clinician or patient may pre-program in the IPG or ETS prior to execution of the stimulation program 100.

It can be sensible to start either at the beginning 183 or middle 182 of the interrupted sub-program (e.g., $102_5$), and different factors may determine which starting point will be used. For example, if the interruption of the stimulation program 100 has occurred for a long time, such as longer than a threshold of 12 hours, it may be beneficial to start at the beginning 183 of interrupted sub-program $102_5$ to allow that sub-program to properly wash back in. By contrast, if the interruption is short, such as less than the 12 hour threshold, it may be reasonable to begin in the middle 182 where sub-program $102_5$ was interrupted. In another example, whether to begin at the beginning 183 or middle 182 of the interrupted sub-program $102_5$ may depend on how far that sub-program was in its execution (e.g., X %). For example, if X is less than a threshold, it may be reasonable to start at the beginning 183, because the sub-program $102_5$ was not very far along in its execution anyway. If X is greater than a threshold, it may be reasonable to start in the middle 182, because the sub-program $102_5$ was already relatively close to finishing.

Figure 8:
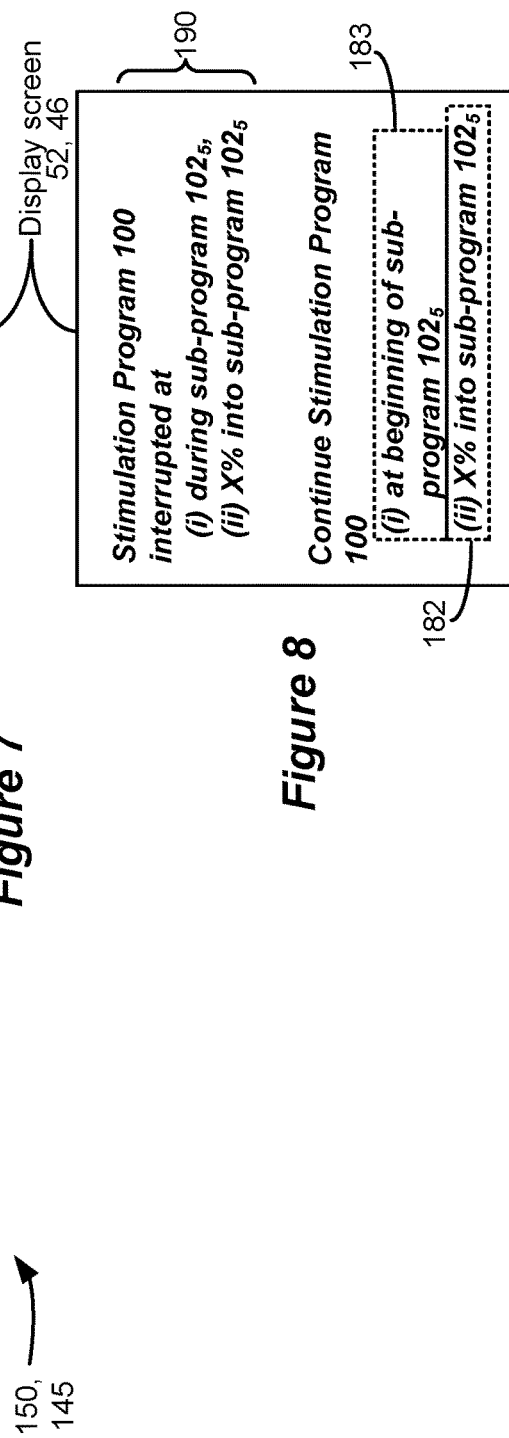
FIG. 8 shows presenting one or more options on an external device to continue execution of an interrupted stimulation program at the beginning of the sub-program during which the interruption occurred, or at the specific point in time during the sub-program where the interruption occurred.

Continuing of execution of the stimulation program 100 may not be automatic in the IPG 110 or ETS 140, and instead may only commence upon receipt of permission from the clinician or patient. For example, when the interrupt 178 is removed, the IPG 110 or ETS 140 can attempt to establish a communication session with the clinician program 150 or external controller 145. Once a communication link is established, the IPG 110 or ETS 140 can send the contents of current status register 184 to the relevant external device 150 or 145 and present the clinician or patient with a notification 190 such as that shown in FIG. 8. This notification 190 can inform the user, using the information in register 184, that the stimulation program 100 was interrupted (i) during sub-program $102_5$, or may further inform the user that (ii) sub-program $102_5$ was interrupted X % into its execution. Based on this notification 190, the user can then choose an option to continue stimulation program 100 (i) at the beginning of sub-program $102_5$ (183), or (ii) X % into sub-program $102_5$ (182). As just discussed, there can be logic to continuing execution at either of these points in time.

Data received at the clinician programmer 150 or external controller 145 can also be used to assess the stimulation program 100 after its completion, and to identify sub-programs $102_i$ in the stimulation program 100 that are beneficial for the patient. As shown in FIG. 7, control circuitry 181 in the clinician programmer 150 or external controller 145 can include stimulation program assessment logic 186 that can be used to automatically select sub-programs $102_i$ that are beneficial, and to discard sub-programs $102_i$ that are not. While stimulation program adjust logic 186 can be configured in different ways, the illustrated example allows each sub-program $102_i$ to be assessed using a pain threshold (Pt) 174 and using power assessment logic 188.

Figure 9:
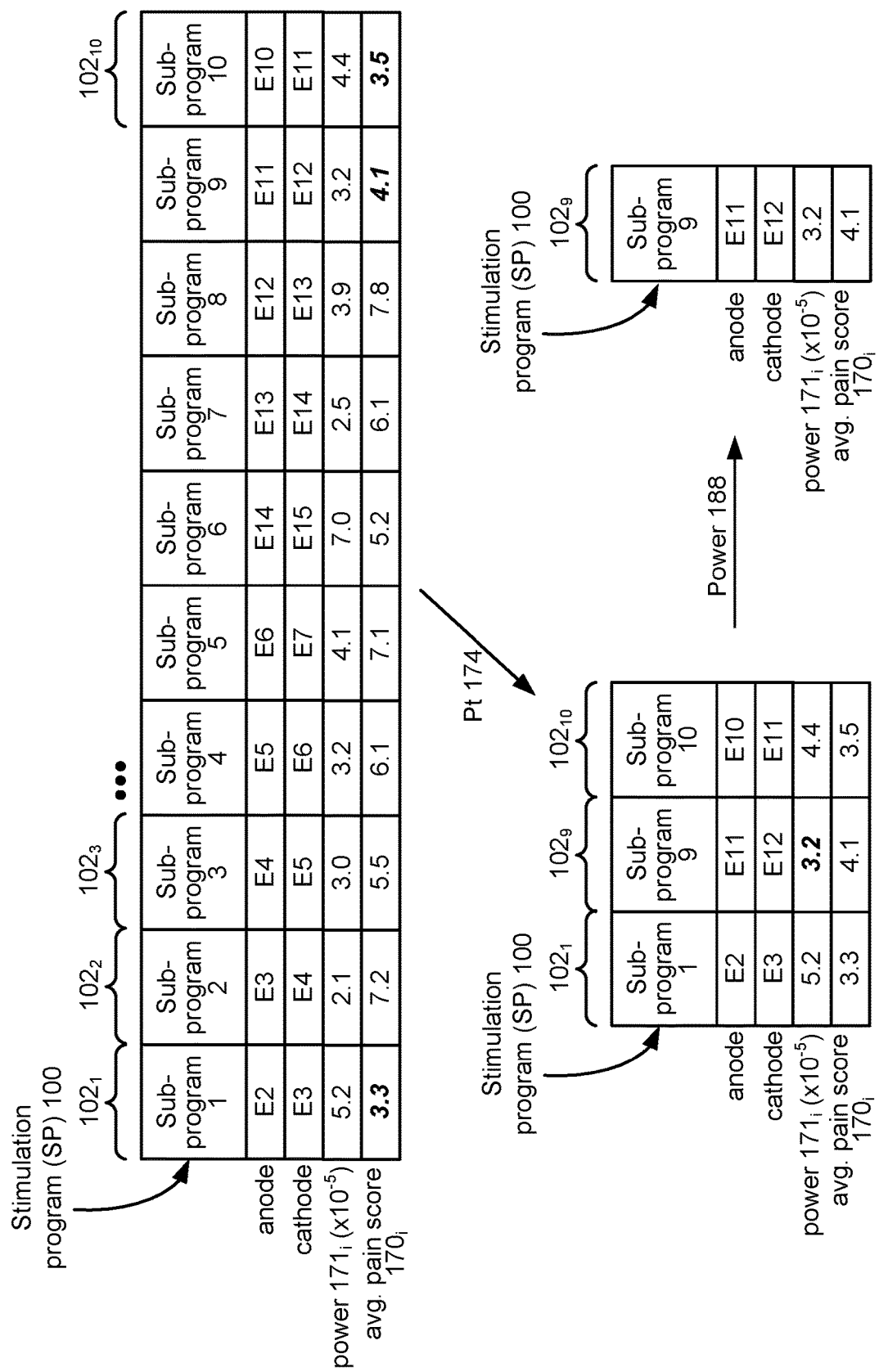
FIG. 9 shows the operation of stimulation program assessment logic on an external device to select sub-programs within the stimulation program that are effective for the patient, and to discard sub-programs within the stimulation program that are not effective for the patient.

An example of how the stimulation program assessment logic 186 can be used to assess the stimulation program 100 is shown in FIG. 9. Shown are the results of stimulation program 100 after its execution, including for each sub-program $102_i$ the average pain score $170_i$ and the power draw $171_i$, which information can be pulled from evaluation memory 172 in the external device (FIG. 7) as discussed previously. Suitable sub-programs $102_i$ are first assessed using the pain threshold (Pt) 174. In this example, the pain threshold is set to a 5, such that sub-programs $102_i$ having an average pain score $170_i$ higher than this threshold are discarded as being ineffective for the patient, while sub-programs $102_i$ having an average pain score $170_i$ lower than this threshold are retained as being effective for the patient. In the example shown, use of the pain threshold 174 causes sub-programs $102_2$ to $102_8$ to be discarded, while sub-programs $102_1$, $102_9$, and $102_{10}$ are kept because they have suitably low average pain scores (3.3, 4.1, and 3.5 respectively).

Thereafter, the remaining sub-programs $102_1$, $102_9$, and $102_{10}$ are assessed using power assessment logic 188 to further identify at least one sub-program $102_i$ that is suitable for the patient based on its power draw. In the example shown, power assessment logic 188 picks the remaining sub-program $102_1$, $102_9$, or $102_{10}$ that has the lowest power draw—in this example, sub-program $102_9$. This simple example assumes that all remaining sub-programs are equally effective (or at least, are effective) for the patient, and thus the best of those remaining sub-programs is the one with the lowest power draw and thus the one that will be most considerate of the IPG 110 or ETS 140's battery. However, this is not strictly required, and instead selection of a single best sub-program $102_i$ can involve weighing the average pain score $170_i$ and power draw $171_i$ in different fashions. Further, operation of the stimulation program assessment logic 186 can select a plurality of sub-programs $102_i$ as being effective for the patient, rather than just one. Stimulation program assessment logic 186 can additionally assess the sub-programs $102_i$ based on factors beyond pain control effectiveness and power draw. In any event, remaining sub-programs $102_i$ can comprise therapeutic stimulation programs that the patient can choose to use, or can comprise a starting point for the discovery of further stimulation programs, as described earlier.

Figure 10A:
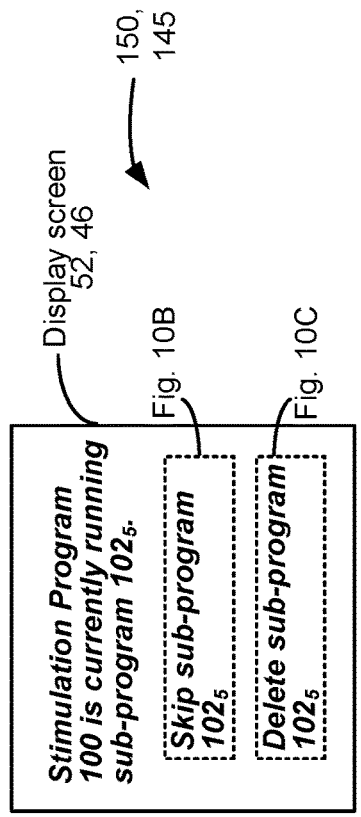
FIGS. 10A-10C show the ability using an external device to skip or delete the execution of a sub-program within the stimulation program.
Figure 10B:
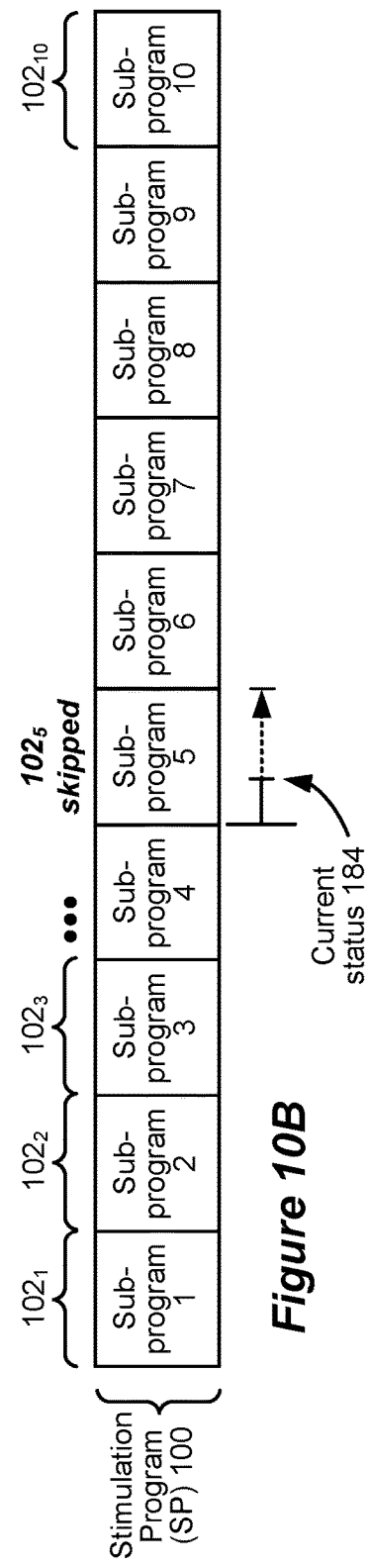
Figure 10C:
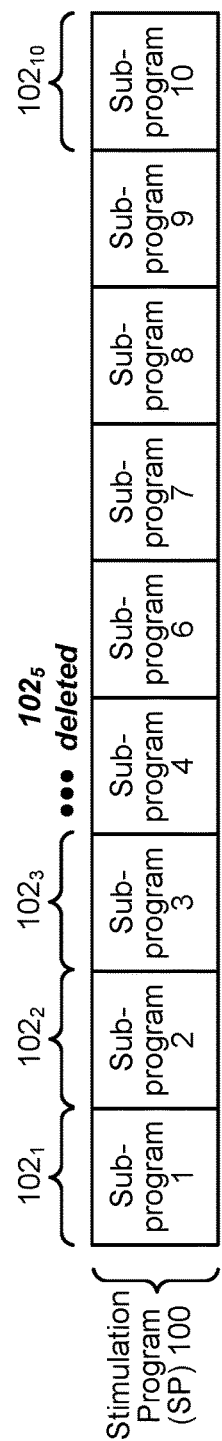

It is preferable that all sub-programs $102_i$ constructed as part of stimulation program 100 be executed and that patient feedback—pain scores $140_j$—be received for each. However, this is not strictly necessary, and it can be useful to allow the patient or clinician to change the execution of the stimulation program 100. This is shown in FIGS. 10A-10C. In FIG. 10A, the user has selected an option on the clinician programmer 150 or external controller 145 to display the sub-program $102_i$ (e.g., $102_5$) that is currently being executed. Further provided are options that can be used to skip or delete this current sub-program $102_5$. This can be useful because this current sub-program may be providing poor results for the patient; for example, the patient may be experiencing significant pain or other side effects from the therapy that sub-program $102_5$ provides, so much so that it is not worth allowing this sub-program to finish its duration.

FIG. 10B shows the effect of skipping sub-program $102_5$. When this option is selected, the clinician programmer 150 or external controller 145 sends an instruction to the IPG 110 or ETS 140 to ignore any remaining duration (d5) that sub-program $102_5$ may have, and to cause program memory 162 (FIG. 6) to send the stimulation parameters for next sub-program $102_6$ to the stimulation circuitry 28 for execution.

FIG. 10C shows the effect of deleting sub-program $102_5$. This option will also send an instruction to the IPG 110 or ETS 140 to cause program memory 162 (FIG. 6) to send the stimulation parameters for next sub-program $102_6$ to the stimulation circuitry 28 for execution, but will additionally delete sub-program $102_5$ from the program memory 162. Deletion of a sub-program will preferably also delete that sub-program from the stimulation program 100 as stored on the relevant external device 150 or 145 itself. Note that deletion of a sub-program $102_i$ may also occur before or after the execution of stimulation program 100 in the IPG 110 or ETS 140.

Computer instructions used in the external devices 145 and 150, including those used to create the stimulation program 100 and its sub-programs $102_i$, to render and receive inputs from the GUIs, and those used by the control circuitry 181, can be stored on a non-transitory computer readable media, such as a solid state, optical, or magnetic memory, and can be loaded into the relevant external device from an external source, e.g., as downloaded from an Internet Server.

Although disclosed to this point in the context of a stimulator device that provides electrical stimulation to a patient's neural tissue, it should be understood that the disclosed invention can have applicability to stimulation of neural tissue involving non-electrical mechanisms. For example, and as disclosed for example in U.S. Patent Application Publication 2017/0281927, optical stimulation may be provided to neural tissue using light (or EM radiation more generally), with the device's "electrodes" providing optical energy to the tissue instead of electrical energy. Still other forms of stimulation can be used as well, including chemical stimulation, magnetic stimulation, thermal stimulation, mechanical stimulation, etc.

Figure 11:
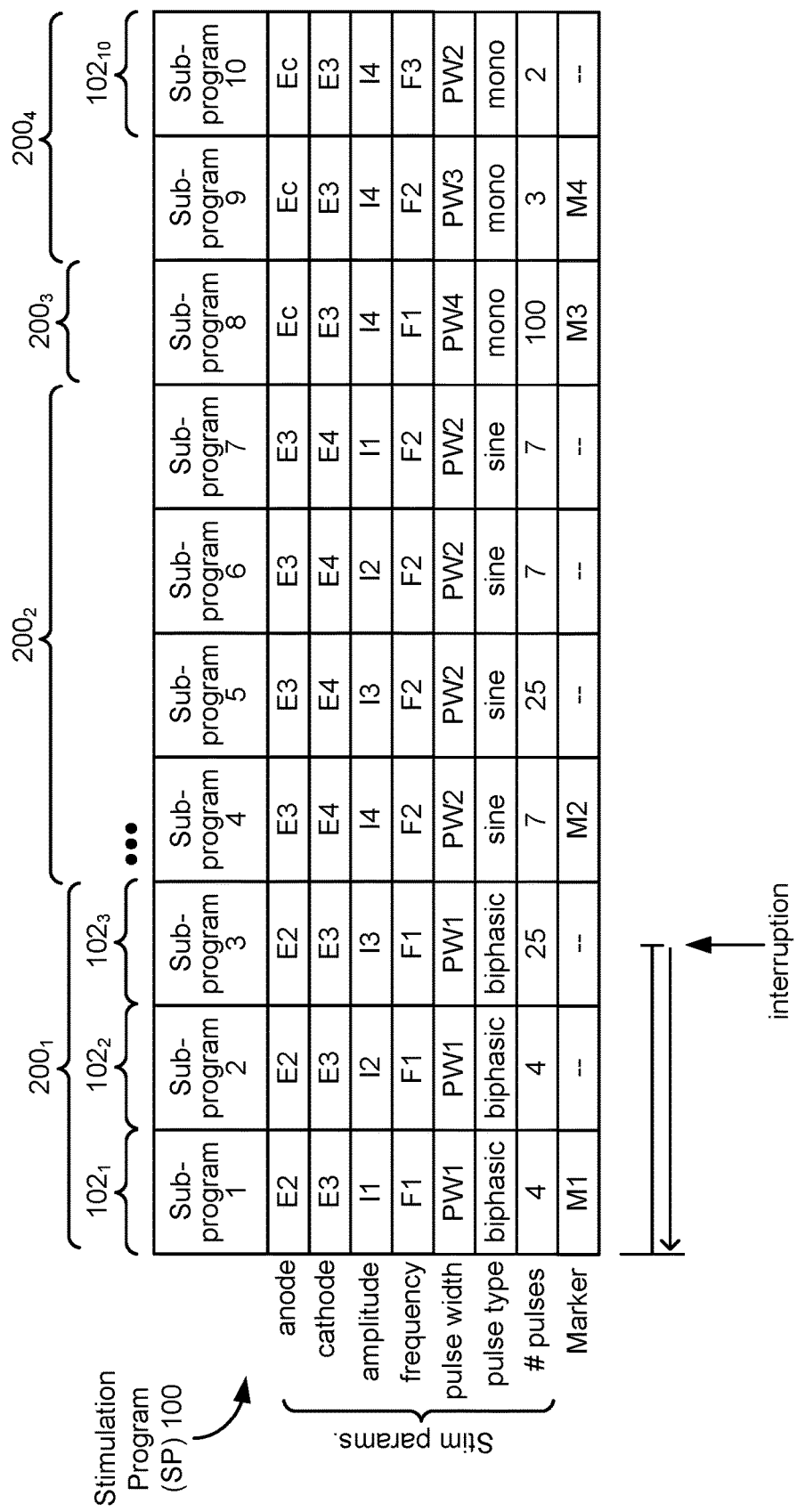
FIGS. 11-12 show another example of a stimulation program and associated IPG or ETS circuitry in which the stimulation program can be pre-defined with markers informing the IPG or ETS of where execution of the stimulation program can continue execution after an interruption.
Figure 12:
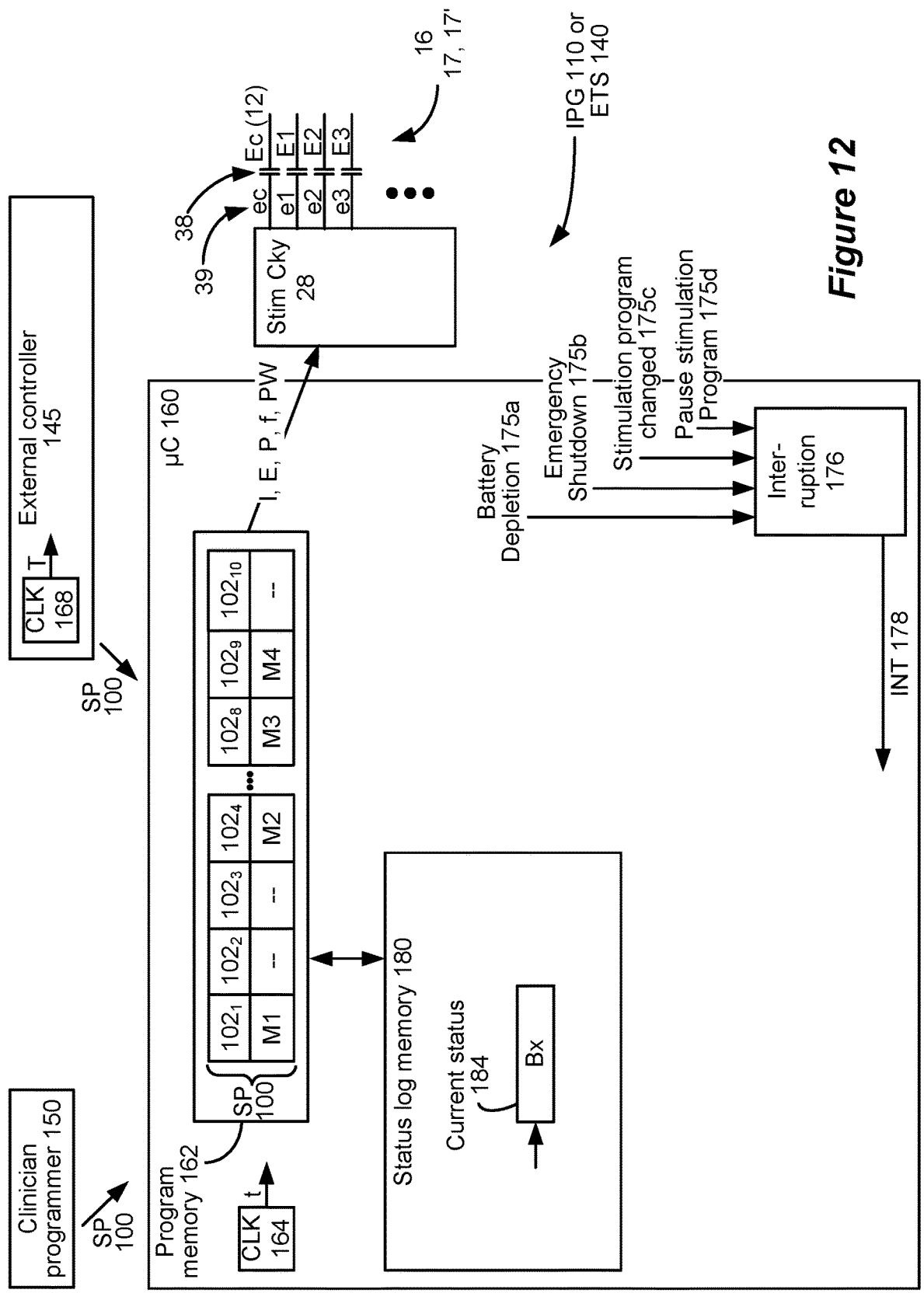

FIGS. 11 and 12 show another example of how the IPG of ETS 140 can track progress of a stimulation program 100, and how the program can be continue execution at a logical point after experiencing an interruption. In this example, the stimulation program, or more specifically certain of its sub-programs $102_i$, can contain markers Mx to inform the IPG 110 or ETS 140 as to where to begin after an interruption. In other words, in this example, the starting points are pre-defined in the stimulation program 100 and/or its sub-programs $102_i$. Further, this example shows that the disclosed technique is not limited to assessment of sub-threshold therapies, and instead shows implementation of the technique using sub-programs $102_i$ with random types of pulses which may be sub- or supra-threshold. This example omits for clarity the additional feature of allowing a patient to associate a pain score with each sub-program, as this feature is not strictly necessary in all examples, although this feature could also be used in this example as described above.

FIG. 11 shows a stimulation program 100 defined by sub-programs $102_i$ that as before will be sequentially executed by the IPG 110 or ETS 140. In this example, the sub-programs $102_i$ may be grouped into blocks $200_i$, with each block including one or more sub-programs. For example, block $200_i$ includes sub-programs $102_i$-$102_3$; block $200_2$ includes sub-programs $102_4$-$102_7$; block $200_3$ includes sub-program $102_8$; and block $200_4$ includes sub-programs $102_9$-$102_{10}$. Each of the blocks $200_i$ may have pulses that are similar in nature, but varying with respect to one or more stimulation parameters. For example, block $200_1$ is used via its sub-programs $102_1$-$102_3$ to form pulses that are biphasic at electrodes E2 (anode) and E3 (cathode), and with a common frequency F1 and pulse width PW1. However, the amplitude of the pulses differs during each of the sub-programs, increasing from I1 in $102_1$ to I2 in $102_2$ and I3 in $102_3$. Moreover, the number of pulses formed during each sub-program can also be specified, with 4 pulses in $102_1$, 4 pulses in $102_2$, and 25 pulses in $102_3$. Pulses as defined by block $200_1$—with increasing amplitudes—can be useful to define as it can allow therapy to ramp up during the provision of the block, thus easing the onset of therapy to the patient.

Block $200_2$ is used via its sub-programs $102_3$-$102_7$ to form pulses with a sinewave shape at electrodes E3 (anode) and E4 (cathode), and with a common frequency F2 and pulse width PW2. However, the amplitude of the pulses differs during each of the sub-programs, decreasing from I4 in $102_4$ to I3 in $102_5$ to I2 in $102_6$ and to I1 in $102_7$. Block $200_2$ may also have different numbers of pulses formed during each of its sub-programs $102_3$-$102_7$ as shown. Blocks $200_3$ and $200_4$ specify monopolar pulses ("mono") which involve the use of the case electrode Ec. It is not however required that the sub-programs $102_i$ within a block $200_i$ have pulses that are similar in nature (e.g., increasing or decreasing in amplitude), and instead the stimulation parameters for sub-programs within a block may simply be random.

A stimulation program 100 such as illustrated in FIG. 11 can be defined at the GUI of an external device such as the clinician programmer 150 or external controller 145, and telemetered to the IPG 110 or ETS 140 as before. In this regard, FIG. 11 may also generally represent the GUI of such external devices, which provides inputs to allow the clinician to define the sub-programs $102_i$ by entering or adjusting the stimulation parameters, and in particular provides one or more inputs to allow the clinician to define which sub-programs should be marked with a marker Mi. In a preferred example, such stimulation programs 100 can be defined using the techniques and systems disclosed in U.S. Patent Application Publication 2018/0071513, which is incorporated herein by reference. Because in FIG. 11 stimulation parameters indicative of the duration of the sub-programs $102_i$ are effectively dictated by virtue of other timing-related stimulation parameters (e.g., frequency, pulse width, number of pulses, etc.), the sub-programs $102_i$ may not be explicitly associated with a duration (di) as in the earlier example (FIG. 5).

The blocks $200_i$ include a marker Mx, which may be stored with or associated with each sub-program $102_i$ within a block, or which (as shown) may only be stored with or associated with only the first sub-program in a block. Effectively, each marker is associated with one of the blocks of sub-program(s): marker M1 is associated with block $200_1$ (sub-programs $102_{1-3}$), M2 with $200_2$ ($102_{4-7}$); M3 with $200_3$ ($102_8$); and M4 with $200_4$ ($102_{9-10}$). Each marker Mx informs the IPG or 110 or ETS 140 where the stimulation program will continue execution once a condition leading to an interruption has been removed, as explained further below. As shown in FIG. 12, these markers can be stored in the program memory 162 of the IPG 110 or ETS 140 along with the other stimulation parameters used by the stimulation circuitry 28.

When a sub-program or block is executed, a marker associated with that sub-program or block can be stored in the current status register 184, which will inform the IPG 110 or ETS 140 where to continue execute after an interrupt condition is removed. For example, when sub-program $102_1$ begins execution, marker M1 is stored in the current status register. The marker can comprise any indicator that informs the IPG 110 or ETS 140 of the sub-program or block with which it is associated, such as a pointer to an address where sub-program $102_1$ can be located in the program memory 162. After execution of sub-program $102_1$ is complete and sub-program $102_2$ begins, a new marker (if any) will be stored in the current status register 184. In the example shown, sub-program $102_2$ is not associated with a new marker, or is associated with the same marker as sub-program $102_1$ by virtue of being in the same block $200_1$. Therefore, marker M1 remains in the current status register 184, and the same occurs when sub-program $102_3$ is executed. When sub-program $102_4$ in a new block $200_2$ is executed, a new marker M2 is stored in current status register 184, and so on.

When the condition (e.g., battery depletion, emergency shutdown, etc.) causing an interruption (INT 178) in the execution of stimulation program 100 is removed, the current status register 184 is read, and in association with the program memory 162 continues execution at a point corresponding to the interruption. In this example, this point comprises the beginning of the block $200i$ in which the interruption occurred, or more specifically at the start of a first sub-program $102i$ in the block. For example, if an interruption occurs during any of sub-programs $102_{1-3}$ in block $200_1$, continued execution of the stimulation program will begin at the beginning of block $200_1$, i.e., at the beginning of sub-program $102_1$. Allowing the user or clinician to pre-define such markers in the stimulation program 100 can be beneficial, and resuming stimulation at marker M1 provides a good example. The point of block $200_1$, as described earlier, is to provide pulses that via sub-programs $102_{1-3}$ increase over time, as this eases the introduction of therapy to the patient. If as in FIG. 11 an interruption occurs during sub-program $102_3$, when the amplitude is highest, resuming execution of the stimulation program at the start of this sub-program $102_3$ might be jarring to the patient. Thus, a user or clinician compiling a stimulation program can use markers Mx to pre-define sensible or therapeutically-beneficial points where stimulation program 100 execution can be continued after its interruption.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method operable with a spinal cord stimulator (SCS) device, wherein the SCS device comprises a plurality of electrodes implanted within a spinal column of the patient, the method comprising:
   executing in the SCS device a stimulation program comprising a plurality of sub-programs thereby sequentially executing each of the sub-programs, wherein each sub-program provides stimulation to one or more of the electrodes using different stimulation parameters;
   receiving at an external system in communication with the SCS device at least one pain score from the patient for each of the sub-programs, wherein the at least one pain score for each sub-program is indicative of the patient's pain upon receiving the stimulation provided by that sub-program; and
   processing the pain scores at the external system to identify one or more of the sub-programs as suitable for the patient; and
   providing therapeutic stimulation to the patient using the identified one or more of the sub-programs.

2. The method of claim 1, wherein at least some of the sub-programs provide the stimulation to different electrodes of the one or more of the electrodes.

3. The method of claim 1, wherein the stimulation is sub-threshold during at least some of the sub-programs.

4. The method of claim 1, wherein each of the sub-programs is executed for a same duration.

5. The method of claim 1, wherein the external system comprises a patient external controller.

6. The method of claim 5, wherein the pain score from the patient for each of the sub-programs is received at the external controller.

7. The method of claim 6, wherein the pain scores are processed at the external controller to identify the one or more of the sub-programs suitable for the patient.

8. The method of claim 6, wherein the external system comprises a clinician programmer, wherein the pain scores are processed at the clinician programmer to identify the one or more of the sub-programs suitable for the patient.

9. The method of claim 1, wherein processing the pain scores at the external system to identify the one or more of the sub-programs as suitable for the patient comprises comparing the pain scores to a threshold.

10. The method of claim 9, wherein there are a plurality of pain score received for at least some of the sub-programs, and wherein the plurality of pain scores for each sub-program are averaged before being compared to the threshold.

11. The method of claim 1, further comprising assessing at the external system a power draw of the identified one or more of the sub-programs.

12. The method of claim 11, further comprising determining at the external system a best of the identified one of more of the sub-programs, wherein the best sub-program comprises a lowest of the power draws.

\* \* \* \* \*